United States Patent
Dubner et al.

(12)

(10) Patent No.: US 6,969,780 B1
(45) Date of Patent: Nov. 29, 2005

(54) PRODUCTION OF BUTANEDIOL

(75) Inventors: Walter S. Dubner, Wilmington, DE (US); Wilfred Po-sum Shum, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 11/017,588

(22) Filed: Dec. 20, 2004

(51) Int. Cl.⁷ .............................................. C07C 27/04

(52) U.S. Cl. .................................... 568/862

(58) Field of Search ....................... 568/862

(56) References Cited

U.S. PATENT DOCUMENTS

| | | | |
|---|---|---|---|
| 4,215,077 A | | 7/1980 | Matsumoto et al. |
| 4,826,799 A | | 5/1989 | Cheng et al. |
| 4,879,420 A | * | 11/1989 | Ernst ........................... 568/617 |
| 5,426,250 A | * | 6/1995 | Chen et al. .................. 568/862 |
| 5,874,652 A | * | 2/1999 | Pitchai et al. ............... 568/862 |
| 5,945,570 A | | 8/1999 | Arhancet et al. |
| 6,225,509 B1 | | 5/2001 | Dubner et al. |

* cited by examiner

*Primary Examiner*—Michael L. Shippen
(74) *Attorney, Agent, or Firm*—William C. Long

(57) ABSTRACT

The catalytic hydrogenation of HBA and/or HMPA is improved by either or both of (1) increasing the temperature in the hydrogenation zone from about 50 to 70° C. at the inlet to above 80° C. at the outlet and (2) raising the pH of the hydrogenation feed to 4.5–6.0 before hydrogenation.

6 Claims, 1 Drawing Sheet

PRODUCTION OF BUTANEDIOL

BACKGROUND OF THE INVENTION

1. Field of the Invention

The present invention relates to the fixed bed catalytic hydrogenation of 4-hydroxybutyraldehyde to 1,4-butanediol and/or to the fixed bed catalytic hydrogenation of 2-methyl 3-hydroxypropionaldehyde to 2-methyl 1,3-propandiol.

2. Description of the Prior Art

A commercial route to 1,4-butanediol (BDO) comprises the carbonylation of allyl alcohol to 4-hydroxybutyraldehyde (HBA) and the hydrogenation of HBA to BDO. Patents which are illustrative of this technology include U.S. Pat. No. 6,225,509 and the patents cited therein. Generally, in the allyl alcohol carbonylation some 2-methyl 3-hydroxypropionaldehyde (HMPA) is formed and this can subsequently be hydrogenated to 2-methyl 1,3 propanediol (MPD).

Problems are encountered in each of the hydrogenation steps especially where fixed bed hydrogenation procedures are used. The fixed bed catalyst tends to deactivate and physically deteriorate with time and as a result slurry hydrogenation procedures have been the norm. For economic reasons the development of successful fixed catalyst bed procedures would be distinctly advantageous.

SUMMARY OF THE INVENTION

In accordance with the present invention, the fixed bed hydrogenation of HBA to BDO and/or HMPA to MPD is carried out using either or both of (1) establishing a hydrogenation temperature profile in the hydrogenation zone such that the inlet section of the hydrogenation zone is maintained at a relatively low temperature and temperature is increased in the direction of reactant flow, and (2) raising the pH of the hydrogenation feed such as by the provision of a buffering agent or by other means, to the level at which catalyst deactivation and deterioration is substantially reduced.

DESCRIPTION OF THE DRAWING

The attached drawing is a graphical representation of the effect of hydrogenation feed pH on loss of nickel from the catalyst.

DETAILED DESCRIPTION

Figure 1:
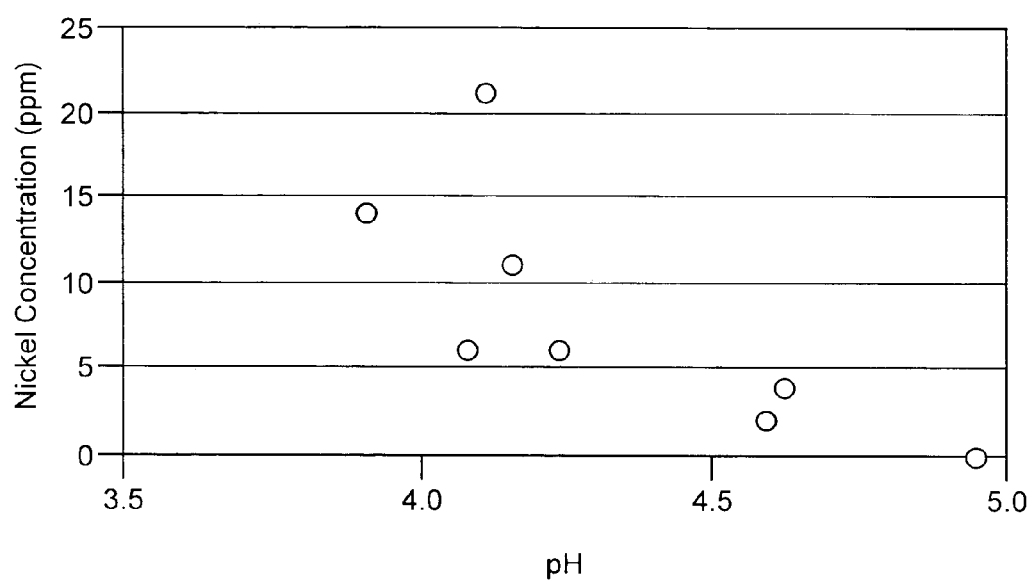

The HBA and/or HMPA which is hydrogenated in accordance with the invention is that which results from the carbonylation of allyl alcohol in accordance with known procedures. In general, such procedures involve the hydroformylation of allyl alcohol using a catalyst such as rhodium and a trisubstituted phosphine or bidentate phosphine ligand in an organic solvent to produce an HBA—containing reaction mixture which also contains substantial HMPA. The reaction mixture is usually contacted with an aqueous extraction liquid to separate HBA and HMPA in aqueous solution from a catalyst—containing organic solvent solution which can be recycled to the hydroformylation. See, for example, U.S. Pat. Nos. 4,215,077, 6,225,509 and the like, the disclosures of which are incorporated herein. The HBA and HMPA containing aqueous solution is then treated in accordance with the present invention to produce BDO and MPD.

The aqueous solutions which are subjected to fixed bed hydrogenation in accordance with the invention generally comprise by weight about 1 to 40% HBA, 0.25 to 10% HMPA, minor amounts of other oxygenated materials from the hydroformylation, traces of hydroformylation catalyst, and 45 to 80% water. Some BDO can be present as in the case of recycle operation but such BDO acts simply as a diluent.

The hydrogenation catalyst which is used, can be any of those based upon Group VIII metals such as, nickel, especially containing molybdenum and/or iron promoters. Nickel catalysts, including bulk, supported and fixed-bed forms, provide acceptable activities and selectivities at moderate cost. Suitable catalysts are commercially available. U.S. Pat. Nos. 4,826,799 and 5,945,570 relate to such catalysts.

In one aspect, the invention involves passing the HBA and/or HMPA—containing aqueous solution and hydrogen through a bed of hydrogenation catalyst which is operated in substantially adiabatic fashion at reaction conditions. The temperature of the solution entering the hydrogenation bed is maintained below about 80° C., for example in the range 30–70° C. The hydrogenation is exothermic, and due to the hydrogenation exotherm, the temperature of the reaction solution increases as it passes through the hydrogenation bed exiting at a temperature higher than that of the feed, illustratively at 80° C. or higher. Other temperature regulatory means can be used such as appropriate provision of external heat transfer media, electrical wrapping, and the like.

It has been found that through the provision of this temperature profile, i.e. a temperature as low as practical at the inlet and substantially higher at the outlet, significantly reduced catalyst deactivation with time is achieved. Through practice of the invention the effective catalyst life has been extended from less than 75 days to over 220 days.

The temperature profile necessary in accordance with the invention can be achieved by conventional temperature control means although simple adiabatic operation wherein the temperature of the catalyst bed increases in the direction of reaction mixture flow due to the exothermic nature of the reaction is preferred. In appropriate practice the feed temperature is maintained below 80° C., i.e. 30–70° C., external cooling can be provided if needed and the exit reaction mixture temperature is above 80° C., preferably in the range of 80 to 105° C. or higher.

It has also been found that process improvements are achieved when the pH of the hydrogenation feed is increased to about 4.5 to 6.0 prior to hydrogenation. Normally, the unbuffered feed solution produced as above indicated has a pH of about 4, and at this value there tends to be substantial loss of active catalyst metal and physical deterioration of the solid catalyst in the fixed catalyst bed hydrogenation zone. It has been found that by increasing the pH of the HBA and/or HMPA hydrogenation feed solution to a pH in the range of 4.5–6.0, preferably in the 4.5–5.5 range, significant process improvements in terms of selectivity and catalyst life are achieved. A preferred method for adjusting the pH is by the addition of a suitable buffer, a preferred buffer being Na OAc/HOAc although other buffers can also be used including citric acid/sodium citrate buffer mixtures.

Other pH adjustment means can be used. For example, the feed solution can be contacted with an adsorbent or ion exchange resin to achieve the necessary pH adjustment.

It should be further noted that it is frequently advantageous in the practice of the invention to dilute the HBA and/or HMPA concentration in the hydrogenation feed solution by dilution with a portion of the hydrogenation effluent.

Although each of the embodiments of temperature profile regulation and feed pH adjustment can individually be used, best results are achieved when both are employed.

The following examples will illustrate the important improvements which are achieved through practice of the invention.

Tests 2 and 3 were conducted using a double-pipe tubular reactor. A thermowell ran down in the center, and through the packed bed of catalyst. The important reactor cross sectional dimensions were: 1.032" reactor tube ID and 0.25" thermowell OD. These dimensions provided 12.5 cm particle diameters (1/16") across, and 5.1 cm$^2$ cross-sectional area.

A 14" long catalyst bed was roughly centered in the middle of the 3' long reactor. 3 mm glass bead filled sections (sandwiched between thin layers of glass wool) were used to support both ends of the catalyst bed. Three thermocouples were positioned in the thermowell running down the center of the reactor bed: at the start, middle and exit of the bed.

The bed size for Examples 2 and 3 was 181 cc of catalyst, which was estimated to provide 1 year's catalyst life at 120 cc/h hydrogenation fresh feed rate. In Example 1 a stainless steel tube having 0.805 inch ID was used and the catalyst bed was 12 inches. Catalyst volume was 100 cc, 1/8 inch catalyst spheres were used, feed rate was 2.5 hr$^{-1}$ LHSV.

COMPARATIVE EXAMPLE 1

In this example molybdenum promoted nickel catalyst was used in the fixed bed system and was fed typical hydroformylation product containing about 18% HBA and 3% HMPA by weight, with small amounts of organic materials, the remainder being water. A uniform temperature profile of 100° C. was maintained by heat wrapping, the system pressure was 750 psi operating pressure. Using an end-of-run criterion of maintaining over 99.9% HBA conversion, the reaction system successfully processed 2.1 liters of feed per gram of catalyst in a test that spanned 75 days.

EXAMPLE 2

In this example which is according to the invention, similar to Comparative Example 1, a molybdenum promoted nickel catalyst was used in a fixed bed system and was fed typical hydroformylation product containing roughly 18% HBA and 3% HMPA by weight with small amounts of organic materials, the remainder being water. The feed temperature was 60° C. and a gradually increasing temperature over the reactor to 92° C. at the exit was maintained. Reaction pressure was 400–750 psi operating pressures. Using an end-of-run criterion of maintaining over 99.9% HBA conversion the reaction system successfully processed over 3.5 liters of feed per gram of catalyst in a test that spanned over 220 days.

A comparison of the results achieved in Example 2, i.e. 220 days of operation, compared with the 75 day run time of Comparative Example 1 clearly illustrates the important advantages achieved by the temperature profile regulation according to the invention.

EXAMPLE 3

In this example various levels of a sodium acetate/acetic acid buffer solutions were added to the hydroformylation product feed having a pH of about 4 and containing roughly 18% HBA and 3% HMPA by weight as described in Example 2. Nickel concentration in the reactor effluent was measured as an indication of catalyst loss during a run similar to that of Example 2. FIG. 1 shows the effect of controlling pH of the feed on nickel dissolution and loss. At a feed pH of 4, the nickel concentration in the effluent was 14–21 ppm. Above a feed pH of 4.5, nickel concentrations in the effluent was below 5 ppm.

A buffer stock solution was made comprised of 130 g sodium acetate trihydrate and 10 g glacial acetic acid together with water to form 1 liter of solution. Buffer was added in amount sufficient to achieve the indicated pH.

These results show the dramatic decrease in loss of active catalyst which results from the pH regulation in accordance with the invention.

The hydrogenation catalyst used in comparative Example 1 was prepared by the procedure of U.S. Pat. No. 4,826,799 while the catalyst used in Examples 2 and 3 was prepared in accordance with U.S. Pat. No. 5,945,570. Each catalyst was a nickel catalyst promoted with a minor amount (3–20 wt %) of molybdenum.

Although Comparative Example 1 and Examples 2 and 3 were not performed under precisely the same conditions, it is believed that the comparative results represent a valid indication of advantages achieved through practice of the invention.

We claim:

1. In a process for the hydrogenation of HBA to BDO and/or HMPA to MPD wherein an aqueous solution of HBA and/or HMPA is contacted with hydrogen in a hydrogenation zone by contact with a fixed bed of hydrogenation catalyst at hydrogenation conditions, the improvement which comprises either or both of (1) maintaining the temperature of the aqueous feed to the hydrogenation zone at about 50 to 70° C. and increasing the temperature of the hydrogenation reaction mixture in the hydrogenation zone to an exit temperature of about 80 to 110° C., and/or (2) adjusting the pH of the aqueous feed to the hydrogenation to a value in the range 4.5–6.0.

2. In a process for the hydrogenation of HBA to BDO and/or HMPA to MPD wherein an aqueous solution of HBA and/or HMPA is contacted with hydrogen in a hydrogenation zone by contact with a fixed bed of hydrogenation catalyst at hydrogenation conditions, the improvement which comprises maintaining the temperature of the aqueous feed to the hydrogenation zone at about 50 to 70° C. and increasing the temperature of the hydrogenation reaction mixture in the hydrogenation zone to an exit temperature of about 80 to 110° C.

3. In a process for the hydrogenation of HBA to BDO and/or HMPA to MPD wherein an aqueous solution of HBA and/or HMPA is contacted with hydrogen in a hydrogenation zone by contact with a fixed bed of hydrogenation catalyst at hydrogenation conditions, the improvement which comprises adjusting the pH of the aqueous feed to the hydrogenation to a value in the range 4.5–6.0.

4. The process of claim 1 wherein the hydrogenation catalyst is a molybdenum promoted nickel catalyst.

5. The process of claim 3 wherein the pH is adjusted by addition of a buffer solution to the aqueous feed.

6. The process of claim 3 wherein the pH is adjusted by addition of a sodium acetate/acetic acid buffer solution to the aqueous feed.

* * * * *